United States Patent [19]

Lösel et al.

[11] 4,452,789
[45] Jun. 5, 1984

[54] 1-FURYL-3,4-DIHYDRO-ISOQUINOLINES

[75] Inventors: Walter Lösel, Gau-Algesheim; Otto Roos, Schwabenheim; Richard Reichl; Franz-Josef Kuhn, both of Gau-Algesheim, all of Fed. Rep. of Germany

[73] Assignee: Boehringer Ingelheim KG, Ingelheim am Rhein, Fed. Rep. of Germany

[21] Appl. No.: 436,588

[22] Filed: Oct. 25, 1982

[30] Foreign Application Priority Data

Nov. 5, 1981 [DE] Fed. Rep. of Germany ....... 3143876

[51] Int. Cl.³ .................. A61K 31/47; A61K 31/535; C07D 405/04; C07D 413/14
[52] U.S. Cl. ............................. 424/258; 424/248.54; 544/128; 546/144; 549/493; 549/500
[58] Field of Search ................ 546/144; 544/128; 424/258, 248.54, 248.55

[56] References Cited

U.S. PATENT DOCUMENTS 3,457,265  7/1969  Seeger et al. .................. 546/144
4,190,660  2/1980  Siu ............................. 546/144

OTHER PUBLICATIONS

Iwasawa et al., "Japan Jour. Pharmacology," vol. 17, No. 2, 1967, pp. 143-152.

Primary Examiner—Mary C. Lee
Assistant Examiner—James H. Turnipseed
Attorney, Agent, or Firm—Hammond & Littell, Weissenberger & Dippert

[57] ABSTRACT

Compounds of the formula

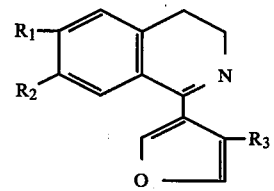

wherein
  $R_1$ and $R_2$, which may be identical to or different from each other, are each hydroxyl or lower alkoxy
  $R_3$ is cyano or —CO—Y;
  Y is hydroxyl, lower alkoxy, or a primary or secondary, substituted or unsubstituted, aliphatic, cycloaliphatic, araliphatic, aromatic or heterocyclic amino group;

and non-toxic, pharmacologically acceptable acid addition salts thereof. The compounds as well as the salts are useful for the treatment of circulatory and coronary disorders.

5 Claims, No Drawings

1-FURYL-3,4-DIHYDRO-ISOQUINOLINES

This invention relates to novel 1-furyl-3,4-dihydroisoquinolines and non-toxic acid addition salts thereof, to methods of preparing these compounds, to pharmaceutical compositions containing them as active ingredients, and to methods of using them for the treatment of circulatory disorders and coronary diseases.

More particularly, the present invention relates to a novel class of compounds represented by the formula

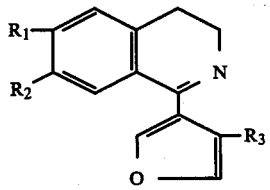

(I)

wherein $R_1$ and $R_2$, which may be identical to or different from each other, are each hydroxyl or lower alkoxy;

$R_3$ is cyano or —CO—Y;

Y is hydroxyl, lower alkoxy, or a primary or secondary, substituted or unsubstituted, aliphatic, cycloaliphatic, araliphatic, aromatic or heterocyclic amino group;

and non-toxic, pharmacologically acceptable acid addition salts thereof.

Preferred compounds are those of the formula I wherein $R_1$ is methoxy;

$R_2$ is methoxy or hydroxyl;

$R_3$ is cyano or —CO—Y,

Y is hydroxyl, alkoxy of 1 to 3 carbon atoms, morpholino, dimethylamino, diethylamino, (alkyl of 1 to 5 carbon atoms)-amino, (B-hydroxy-propyl)-amino, propargyl-amino or —NH—$(CH_2)_n$—R;

n is 1, 2 or 3; and

R is dimethylamino, methoxy, chlorine, morpholino, -methoxy-phenyl, dimethoxy-phenyl or 2-furyl; and non-toxic, pharmacologically acceptable acid addition salts thereof.

A preferred subgenus thereunder is constituted by compounds of the formula

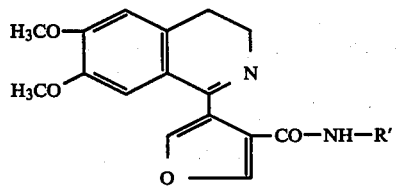

(Ia)

wherein

R' is alkyl of 1 to 5 carbon atoms, di(lower alkyl) amino-lower alkyl or cyano, and non-toxic, pharmacologically acceptable acid addition salt thereof.

An especially preferred subgenus is constituted by compounds of the formula Ia wherein R' is n-propyl, n-butyl or isobutyl, and non-toxic, pharmacologically acceptable acid addition salts thereof.

The compounds embraced by formula I may be prepared by the following methods:

Method A

By cyclizing a furan-3,4-dicarboxylic acid amide of the formula

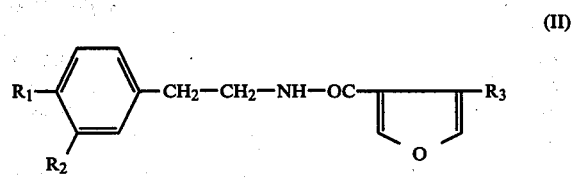

(II)

wherein $R_1$ and $R_2$ and $R_3$ have the meanings previously defined, with an acid cyclizing agent, especially Lewis acid.

Examples of suitable Lewis acids are phosphorus trichloride, phosphorus pentachloride, phosphorus oxychloride, boron trifluoride and tin tetrachloride.

However, strong mineral acids such as sulfuric acid, fluorosulfonic acid, hydrofluoric acid or polyphosphoric acid may also be used.

The acid cyclizing agent is usually provided in excess. The preferred cyclizing agent is phosphorus oxychloride.

The cyclization reaction may be performed in the presence or absence of a solvent. Any inert solvent may be used, provided it has a sufficiently high boiling point and the reactants are sufficiently soluble therein. Examples of suitable solvents are benzene, alkyl-benzenes, chloro-benzenes, decahydronaphthalene, chloroform, methylene chloride, acetonitrile and the like.

A variant of this method consists of using the cyclizing agent itself, such as phosphorus oxychloride, as the solvent medium.

As far as the reaction temperature is concerned, there are no particular limitations. The reaction may be performed within a wide temperature range, preferably while heating the reaction mixture up to the boiling point of the solvent.

Method B

By reacting a 3-[(3,4-dihydro-isoquinolyl-1)]-furan-4-carboxylic acid derivative of the formula

(III)

wherein $R_1$ and $R_2$ have the meanings previously defined, and X is chlorine, methoxy, ethoxy or an imidazolide group, with a compound of the formula

Y—H  (IV)

wherein Y has the meanings previously defined.

This method incorporates, inter alia, the conversion of 1-furyl-3,4-dihydro-isoquinolines of the formulas I and Ia into other end products. Thus, a corresponding carboxylic acid ester or carboxylic acid amide may be converted into a corresponding 3,4-dihydro-isoquinolyl-(1)-furan-4-carboxylic acid. Furthermore, this process provides the possibility of reacting an acid chloride, an ester or an imidazolide of the formula III with a suitable amine of the formula IV to form a compound of the formula I or Ia.

Some of the starting compounds of the formula II are known compounds, while others are novel. They are prepared by reacting a suitable reactive derivative of furan-3,4-dicarboxylic acid with a primary or secondary amine to form directly a compound of the formula II or, alternatively, by first providing a monoamide derivative of furan-3,4-dicarboxylic acid and reacting it as such, or by again converting it into a reactive form, with a further amine in a manner such that a derivative of the formula II is formed.

Examples of furan-3,4-dicarboxylic acid derivatives which are suitable for the preparation of the starting compounds of the formula II are those where the carboxyl groups are converted into acid halides, acid azides or mixed anhydrides, for instance with an aromatic or aliphatic carboxylic acid, alkylcarbonic acid or dialkylphosphoric acid, or are present in the form of active acid amides, for instance with imidazole, 4-substituted imidazole, dimethylpyrazole, triazole, or tetrazole, or as active esters such as cyanomethyl, methoxymethyl, vinyl, propargyl, nitrophenyl, methanesulfonyl, or pyridylalkyl esters, or as esters with dimethyl-hydroxyl-amine, 1-hydroxy-succinimide, 1-hydroxy-benztriazole, dicyclohexyl-urea, etc.

The preferred furan-3,4-dicarboxylic acid derivative is furan-3,4-dicarboxylic acid monoethyl ester chloride.

The amide formation is, as a rule, performed in the presence of a solvent such as dioxane, acetonitrile, tetrahydrofuran, pyridine or any other organic solvent which does not adversely affect the reaction, optionally in the presence of an inorganic or organic base as an acid-binding agent. The solvents may also be used in the form of mixtures. However, if the amine of the formula III is provided in sufficient excess, it may also serve as the solvent medium.

The reaction temperature is not critical; as a rule, the reaction can be performed while cooling, at ambient temperature or while heating.

The starting compounds of the formula III may be prepared from the corresponding 3-[(3,4-dihydro-isoquinolyl-1)]-furan-4-carboxylic acids.

The compounds of the formula I are basic substances and therefore form addition salts with inorganic or organic acids. Examples of non-toxic, pharmacologically acceptable acid addition salts are those formed with hydrochloric acid, hydrobromic acid, hydroiodic acid, hydrofluoric acid, sulfuric acid, phosphoric acid, nitric acid, acetic acid, propionic acid, butyric acid, caproic acid, valeric acid, oxalic acid, malonic acid, succinic acid, maleic acid, fumaric acid, lactic acid, tartaric acid, citric acid, malic acid, benzoic acid, p-hydroxy-benzoic acid, p-amino-benzoic acid, phthalic acid, cinnamic acid, salicylic acid, ascorbic acid, 8-chlorotheophylline, methanesulfonic acid or the like.

The following examples illustrate the present invention and will enable others skilled in the art to understand it more completely. It should be understood, however, that the invention is not limited solely to the particular examples given below.

PREPARATION OF STARTING COMPOUNDS

EXAMPLE A

Furan-3,4-dicarboxylic acid monoethyl ester

A solution of 235 gm of furan-3,4-dicarboxylic acid diethyl ester and 62.1 gm of potassium hydroxide in 800 ml of 60% ethanol was stirred for 2 hours at room temperature, and then the solvent was distilled off in vacuo. The residue was acidified by carefully adding an aqueous $KHSO_4$ solution dropwise thereto, while stirring, and the monoester was extracted with methylene chloride and crystallized from ethyl acetate/petroleum ether.

Yield: 169.3 gm (83% of theory).

EXAMPLE B

Furan-3,4-dicarboxylic acid monoethyl ester chloride

A mixture of 183 gm of furan-3,4-dicarboxylic acid monoethyl ester and 119 gm of thionyl chloride was refluxed, while stirring, for 90 minutes on a water bath. The excess thionyl chloride was then evaporated in vacuo, and the residue was distilled under reduced pressure (147°–148° C./16 mm Hg), yielding 183.4 gm (91% of theory) of the desired monoester chloride.

EXAMPLE C

3-[(3,4-Dimethoxy-phenyl)-2-ethylaminocarboxyl]-furan-4-carboxylic acid ethyl ester A solution of 295 gm of furan-3,4-dicarboxylic acid monoethyl ester chloride in 500 ml of absolute tetrahydrofuran was added dropwise at room temperature to a cooled mixture of 263 gm of 2-(3,4-dimethoxy-phenyl)-ethylamine, 171 gm of triethylamine and 500 ml of absolute tetrahydrofuran, while stirring. After the reaction had gone to completion, the precipitated triethylammonium chloride was suction-filtered off, the filtrate was evaporated, and the solid residue was taken up in a mixture of water and methylene chloride. The organic phase was dried with sodium sulfate, and the methylene chloride was evaporated, leaving the desired ethyl ester which was recrystallized from ethyl acetate.

Yield: 459 gm (91% of theory); m.p. 90°–92° C.

EXAMPLE D

3-[(3,4-dimethoxy-phenyl)-2-ethylaminocarbonyl]-furan-4-carboxylic acid

A solution of 31.9 gm of 3-[(3,4-dimethoxy-phenyl)-2-ethylaminocarbonyl]-furan-4-carboxylic acid ethyl ester in 150 ml of methanol was admixed with 150 ml of 1 N sodium hydroxide, and the mixture was stirred for 45 minutes at 50° C. The reaction mixture was then neutralized with hydrochloric acid, the solvent was distilled off, and the desired reaction product was extracted from the residue with methylene chloride and crystallized from ethyl acetate/petroleum ether.

Yield: 25.5 gm (87.3% of theory); m.p. 188°–189° C.

EXAMPLE E

3-[(3,4-Dimethoxy-phenyl)-2-ethylaminocarbonyl]-furan-4-carboxylic acid n-propylamide Variant A A solution of 30 gm of 3-[(3,4-dimethoxy-phenyl)-2-ethylaminocarbonyl]-furan-4-carboxylic acid and 16.2 gm of N,N'-carbonyl-diimidazole in 150 ml of absolute tetrahydrofuran was stirred for 1 hour at room temperature under exclusion of moisture.

Thereafter, 7 ml of n-propylamine were added, and the mixture was stirred at room temperature for 4 hours more. The solvent was evaporated in vacuo, the residue was dissolved in methylene chloride, and the solution was washed first with dilute hydrochloric acid and then with water. The organic phase was dried with sodium sulfate, the solvent was evaporated, and the residue was crystallized from ethyl acetate.

Yield: 29.4 gm (87% of theory)

Variant B

A mixture of 63 gm of 3-[(3,4-dimethoxy-phenyl)-2-ethylaminocarbonyl]-furan-4-carboxylic acid ethyl ester and 120 ml of n-propylamine was heated for 24 hours at 120° C. in an autoclave. Thereafter, the reaction mixture was admixed with 300 ml of ethanol and the mixture was boiled in the presence of activated charcoal. After cooling the mixture was suction-filtered, the filtrate was evaporated, and the residue was recrystallized from ethyl acetate/petroleum ether.

Yield: 51 gm (78% of theory).

For higher purity, the residue of the filtrate evaporation may be purified on a silicagel column (methylene chloride:methanol=100:1→100:2) prior to recrystallization.

PREPARATION OF END PRODUCTS OF THE FORMULA I

EXAMPLE 1

3-[3,4-Dihydro-6,7-dimethoxy-isoquinolyl-(1)]-furan-4-carboxylic acid ethyl ester A solution of 50 gm of 3-carbethoxy-furan-4-carboxylic acid [2-(3,4-dimethoxy-phenyl)-ethyl]-amide in 120 ml of acetonitrile was admixed with 18 ml phosphorus oxychloride, and the mixture was refluxed for about 2 hours. Thereafter, the reaction mixture was evaporated, the residue was taken up in 200 ml of methylene chloride, and the solution was made alkaline by stirring it into a solution of potash in ice water. The mixture was extracted with methylene chloride, the organic phase was dried with sodium sulfate, the solvent was evaporated, and the residue was purified on a silicagel column (methylene chloride:methanol=100:1→100:2), yielding 37.5 gm (79% of theory) of the compound of the formula

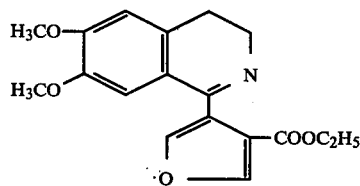

M.p. 151°-153° C.

EXAMPLE 2

3-[(3,4-Dihydro-6,7-dimethoxy-isoquinolyl-(1)]-furan-4-carboxylic acid hydrochloride A solution of 15 gm of 4-[3,4-dihydro-6,7-dimethoxy-isoquinolyl-(1)]-furan-4-carboxylic acid ethyl ester in 50 ml of ethanol was admixed with 45 ml of potassium hydroxide. After about 60 minutes of standing, the mixture was neutralized with hydrochloric acid, the solvent was distilled off, the dry residue was taken up in ethanol, the solution was acidified with ethanolic hydrochloric acid, and the mixture was suction-filtered. The filtrate was evaporated, and the residue was caused to crystallize by adding acetone thereto. Recrystallization from methanol/ether, optionally in the presence of activated charcoal, yielded 13.6 gm (88.4% of theory) of pure product, M.p. 212°-214° C.

EXAMPLE 3

3-[3,4-Dihydro-6,7-dimethoxy-isoquinolyl-(1)]-furan-4-carboxylic acid n-propyl-amide Variant A A solution of 40 gm of 3-(n-propylaminocarbonyl)-furan-4-carboxylic acid [2-(3,4-dimethoxy-phenyl)-ethyl]-amide in 400 ml of acetonitrile was admixed with 25 ml of phosphorus oxychloride, and the mixture was refluxed for about 2 hours. Thereafter, the reaction mixture was evaporated, the residue was taken up in methylene chloride, and the solution was made alkaline by stirring it into a solution of potash in ice water. The mixture was worked up as described in Example 1, and the raw product was purified on a silicagel column (Methylene chloride:methanol=100:1→100:2).

The hydrochloride was prepared by dissolving the free base thus obtained in the least sufficient amount of ethanol, and admixing the solution with ethanolic hydrochloric acid. The hydrochloride was caused to crystallize out by adding absolute ether dropwise to the acid solution.

Yield: 24.1 gm (57% of theory); m.p. 199°-205° C.

Variant B

A mixture of 30.1 gm of 3-[3,4-dihydro-6,7-dimethoxy-isoquinolyl-(1)]-furan-4-carboxylic acid and 60 ml of thionyl chloride was refluxed for 40 minutes. Thereafter, the excess thionyl chloride was distilled off in vacuo, and the residue was added in portions into an ice-cooled solution of 13 gm of n-propylamine in 200 ml of absolute tetrahydrofuran, while stirring. After about 1 hour the reaction mixture was worked up as usual, and the reaction product was purified on a silicagel column and crystallized as its hydrochloride from methanol/ether.

Yield: 16.8 gm (44.5% of theory); m.p. 204°-205° C.

Variant C 33.8 gm of 3-[3,4-dihydro-6,7-dimethoxy-isoquinolyl-(1)]-furan-4-carboxylic acid and 17.2 gm of N,N'-carbonyldiimidazole were dissolved in 150 ml of absolute tetrahydrofuran by refluxing, and after 1 hour the solution was admixed with 7 ml of n-propylamine. The mixture was stirred overnight at room temperature, whereupon the solvent was evaporated in vacuo and the residue was taken up in a mixture of methylene chloride and water. The organic phase was dried and evaporated, and the residue was purified on a silicagel column and crystallized from methanol/ether as its hydrochloride.

Yield: 7.5 gm (15% of theory); m.p. 203°-204° C.

EXAMPLE 4

3-[3,4-Dihydro-6,7-dimethoxy-isoquinolyl-(1)]-furan-4-carboxylic acid nitrile

A mixture of 10 gm of 3-[2-(3,4-dimethoxy-phenyl)-ethylaminocarbonyl]-furan-4-carboxylic acid amide, 50 ml of acetonitrile and 30 ml of phosphorus oxychloride was refluxed for 1.5 hours as in Example 1. Thereafter, the reaction mixture was worked up as usual, the reaction product was purified on a silicagel column, and its hydrochloride was crystallized from methanol/ether.

Yield: 7.8 gm (77% of theory); m.p. 204°–207° C.

The following table shows additional compounds of the formula I which were prepared in analogy to the above examples:

The compounds of the present invention, that is, those embraced by formula I above and their non-toxic, pharmacologically acceptable acid addition salts, have useful pharmacodynamic properties. More particularly, they enhance the blood flow through and the oxygen supply to the tissues, especially in the central nervous system. In addition, the compounds of the present invention have a contractility-increasing and blood pressure-influencing activity component.

| EXAMPLE | $R_1$ | $R_2$ | $R_3$ | M.P. (°C.) | SALT/FORM |
|---|---|---|---|---|---|
| 5. | $CH_3O-$ | $-OH$ | $-COOC_2H_5$ | 173–175 | Base |
| 6. | $CH_3O-$ | $CH_3O-$ | $-CONHCH_3$ | 246 | HCl |
| 7. | $CH_3O-$ | $CH_3O-$ | $-CON(CH_3)_2$ | 167–168 (decomp) | |
| 8. | $CH_3O-$ | $CH_3O-$ | $-CONHCH_2CH_3$ | 212–215 (decomp) | HCl |
| 9. | $CH_3O-$ | $CH_3O-$ | $-CON(CH_2CH_3)_2$ | 203–205 (decomp) | HCl |
| 10. | $CH_3O-$ | $CH_3O-$ | $-CONH(CH_2)_3CH_3$ | 216 (decomp) | HCl |
| 11. | $CH_3O-$ | $CH_3O-$ | $-CONH(CH_2)_4CH_3$ | 215–218 (decomp) | HCl |
| 12. | $CH_3O-$ | $CH_3O-$ | $-CONHCH_2CH(CH_3)_2$ | 195–200 (decomp) | HCl |
| 13. | $CH_3O-$ | $CH_3O-$ | $-CONHCH_2CH_2CH(CH_3)_2$ | 222–225 (decomp) | HCl |
| 14. | $CH_3O-$ | $CH_3O-$ | $-CONH-CH_2-C\equiv CH$ | 244–245 (decomp) | HCl |
| 15. | $CH_3O-$ | $CH_3O-$ | $-CONH(CH_2)_2N(CH_3)_2$ | 162–165 | HCl |
| 16. | $CH_3O-$ | $CH_3O-$ | $-CONH(CH_2)_3N(CH_3)_2$ | 116–125 | HCl |
| 17. | $CH_3O-$ | $CH_3O-$ | $-CONH-CH_2CH_2OCH_3$ | 216–218 (decomp) | HCl |
| 18. | $CH_3O-$ | $CH_3O-$ | $-CONH-CH_2-CH_2-CH_2Cl$ | 233–237 (decomp) | HCl |
| 19. | $CH_3O-$ | $CH_3O-$ | $-CO-NH-CH_2-CH(OH)-CH_3$ | 218–224 (Z) | HCl |
| 20. | $CH_3O-$ | $CH_3O-$ | $-CO-N\!\!\!<\!\!\!\begin{array}{c}\text{morpholino}\end{array}$ (morpholine ring) | 141–144 | HCl |
| 21. | $CH_3O-$ | $CH_3O-$ | $-CO-NH-CH_2CH_2-N(morpholine)$ | 183–185 | HCl |
| 22. | $CH_3O-$ | $CH_3O-$ | $-CONH-CH_2CH_2-$(2-methoxyphenyl) | 221–222 | HCl |
| 23. | $CH_3O-$ | $CH_3O-$ | $-CO-NH-CH_2-CH_2-$(2,5-dimethoxyphenyl) | 194–198 | HCl |
| 24. | $CH_3O-$ | $CH_3O-$ | $-CO-NH-CH_2-CH_2-$(3,4-dimethoxyphenyl) | 186–192 | HCl |
| 25. | $CH_3O-$ | $CH_3O-$ | $-CO-NH-CH_2-$(furan-2-yl) | 231–234 | HCl |

For the stated indications, the compounds of this invention represent a novel class of substances; therefore, they are especially useful in all those instances where the presently available drugs fail.

Furthermore, the compounds of the present invention are useful as intermediates for the preparation of other pharmaceuticals.

The toxicities of the compounds of this invention are generally very low, as determined by p.o. and i.v. administration in mice.

By virtue of the above pharmacological properties the compounds of this invention are useful for the treatment of circulatory and coronary disorders in warm-blooded animals.

For pharmaceutical purposes the compounds of the present invention are administered to warm-blood animals perorally, parenterally or rectally as active ingredients in customary pharmaceutical compositions, that is, compositions consisting essentially of an inert pharmaceutical carrier and an effective amount of the active ingredient, such as tablets, coated pills, capsules, wafers, powders, solutions, suspensions, emulsions, syrups, suppositories and the like. An effective amount of the compounds according to the present invention for oral administration is from 0.5 to 50 mgm/kg body weight, and for i.v. administration it is from 0.01 to 10 mgm/kg body weight, preferably 1 to 5 mgm/kg body weight.

The following examples illustrate a few pharmaceutical compositions comprising a compound of the present invention as an active ingredient and represent the best modes contemplated of using the invention. The parts are parts by weight unless otherwise specified.

EXAMPLES 26

Coated tablets

The tablet core composition is compounded from the following ingredients:

| | |
|---|---|
| 3-[3,4-Dihydro-6,7-dimethoxy-isoquinolyl-(1)]-furan-4-carboxylic acid ethyl ester | 5 parts |
| Lactose | 65 parts |
| Corn starch | 130 parts |
| Secondary calcium phosphate | 40 parts |
| Soluble starch | 3 parts |
| Magnesium stearate | 3 parts |
| Colloidal silicic acid | 4 parts |
| Total | 250 parts |

Preparation

The active ingredient is admixed with a portion of the respective excipients, the mixture is thoroughly kneaded with an aqueous solution of the soluble starch and the moist mass is granulated through a screen. The granulate is dried, admixed with the remainder of the respective excipients, and the composition is compressed into 250 mgm-tablet cores which are subsequently coated with a thin shell consisting essentially of a mixture of sugar, talcum and gum arabic.

EXAMPLE 27

Injection solution

The solution is compounded from the following ingredients:

| | |
|---|---|
| 3-[3,4-Dihydro-6,7-dimethoxy-isoquinolyl-(1)]-furan-4-carboxylic acid hydrochloride | 1.0 parts |
| Sodium chloride | 18.0 parts |
| Distilled water q.s. ad | 2000.0 parts by vol. |

Preparation

The active ingredient and the sodium chloride are dissolved in the distilled water, the solution is filtered into 2 cc-ampules in an atmosphere of nitrogen.

EXAMPLE 28

Drop solution

The solution is compounded from the following ingredients:

| | |
|---|---|
| 3-[3,4-Dihydro-6,7-dimethoxy-isoquinolyl-(1)-furan-4-carboxylic acid n-propylamide | 0.02 parts |
| Methyl p-hydroxy-benzoate | 0.07 parts |
| Propyl p-hydroxy-benzoate | 0.03 parts |
| De-mineralized water | 100.00 parts by vol. |

Preparation

The active ingredient and the p-hydroxy-benzoates are dissolved in the de-mineralized water, the solution is filtered, and the filtrate is filled into 100 cc-bottles equipped with a dropping spout.

Any one of the other compounds embraced by formula I or a non-toxic, pharmacologically acceptable acid addition salt thereof may be substituted for the particular active ingredient in Example 26 through 28. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

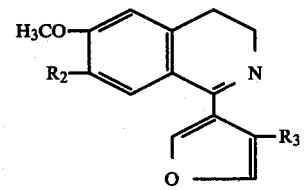

wherein
 $R_2$ is methoxy or hydroxyl;
 $R_3$ is cyano or —CO—Y;
 Y is hydroxyl, alkoxy of 1 to 3 carbon atoms, morpholino, dimethylamino, diethylamino, (alkyl of 1 to 5 carbon atoms)-amino, (-hydroxyl-propyl)-amino, propargyl-amino or —NH—CH$_2$)$_n$R;
 n is 1, 2 or 3; and R is dimethylamino, methoxy, chlorine, morpholino, o-methoxy-phenyl, dimethoxyphenyl or 2-furyl;

or a non-toxic, pharmacologically acceptable acid addition salt thereof.

2. A compound of claim 1, which is of the formula

[Structure: 6,7-dimethoxy-3,4-dihydroisoquinoline with furan-CO-NH-R' substituent]

wherein

R' is alkyl of 1 to 5 carbon atoms, di(lower alkyl)amino-lower alkyl or cyano, or a non-toxic, pharmacologically acceptable acid addition salt thereof.

3. A compound of claim 2, wherein R' is n-propyl, n-butyl or isobutyl, or a non-toxic, pharmacologically acceptable acid addition salt thereof.

4. A pharmaceutical composition for the treatment of circulatory and coronary disorders consisting essentially of an inert pharmaceutical carrier and an effective circulation enhancing amount of a compound of claim 1.

5. The method of treating circulatory and coronary disorder in a warm-blooded animal, which comprises perorally, parenterally or rectally administering to said animal an effective circulation enhancing amount of a compound of claim 1.

* * * * *